United States Patent [19]

Stevenson

[11] Patent Number: 5,681,566
[45] Date of Patent: Oct. 28, 1997

[54] ANTIBODY CONJUGATES WITH TWO OR MORE COVALENTLY LINKED FC REGIONS

[75] Inventor: George T. Stevenson, Southampton, United Kingdom

[73] Assignee: 3i Research Exploitation Limited, United Kingdom

[21] Appl. No.: 456,612

[22] Filed: Jun. 1, 1995

Related U.S. Application Data

[63] Continuation of Ser. No. 678,950, filed as PCT/GB89/01269, Oct. 23, 1989, abandoned.

[30] Foreign Application Priority Data

Oct. 24, 1988 [GB] United Kingdom .................. 8824869

[51] Int. Cl.$^6$ .......................... A61K 39/44; C07K 17/02; C07K 16/46
[52] U.S. Cl. ........................ 424/178.1; 424/179.1; 424/133.1; 424/136.1; 530/391.1; 530/391.3; 530/391.7; 530/391.9
[58] Field of Search .................. 530/391.1, 391.9, 530/391.7, 387.3; 424/133.1, 136.1, 178.1, 179.1

[56] References Cited

U.S. PATENT DOCUMENTS

| | | |
|---|---|---|
| 3,928,580 | 12/1975 | Fontaine . |
| 4,344,938 | 8/1982 | Sedlacek et al. . |
| 4,479,895 | 10/1984 | Auditore-Hargreaves ............ 530/391.1 |
| 4,676,980 | 6/1987 | Segal et al. ........................ 424/136.1 |

FOREIGN PATENT DOCUMENTS

| | | | |
|---|---|---|---|
| 0010309 | 4/1980 | European Pat. Off. ...... | A61K 39/395 |
| 0147283 | 7/1985 | European Pat. Off. ...... | A61K 39/395 |
| 0314317 | 5/1989 | European Pat. Off. ........ | C12N 15/00 |
| 0336379 | 10/1989 | European Pat. Off. ...... | A61K 39/395 |
| WO89/01975 | 3/1989 | WIPO ............................ | C12P 21/00 |

OTHER PUBLICATIONS

J. Siegelman et al, Cell Tissue Res., 248: 599–605 (1987) "Characterization of immunoglobulin G–Fc receptor activity in the outflow system of the cerebrospinal fluid".

T. Kitagawa, et al, Chem. Pharm. Bull. 29(4) 1130–1135 (1981) "Preparation and Characterization of Hetero–bifunctional Cross–linking Reagents for Protein Modifications".

15–Immunochemistry, vol. 110 (1989): 552–553 Abstract No. 210562a.

15–Immunochemistry, vol. 107 (1987) abstract #37765g (of Siegelman et al above).

G.T. Stevenson and M.J. Glennie, Cancer Surveys, vol. 4 No. 1 (1985) "Surface immunoglobulin of B–lymphocytic tumours as a therapeutic target".

M.W. Fanger, et al, Immunology Today, vol. 10, No. 3 (1989) "Cytotoxicity mediated by human Fc receptors for IgG", pp. 92–99.

F.K. Stevenson et al, Br. J. Cancer, 50, 407–413 (1984) "Consumption of Monoclonal Anti–idiotypic Antibody by Neoplastic B Lymphocytes: A Guide for Immunotherapy".

T. J. Elliott et al, The Journal of Immunology, vol. 138, 981–988, Feb. 2, 1987 "Analysis Of The Interaction Of Antibodies With Immunoglobulin Idiotypes On Neoplastic B Lymphocytes: Implications For Immunotherapy".

G.T. Stevenson et al, Bioscience Reports 5, 991–998 (1985) "Preparation and Properties of FabIgG, a Chimeric Univalent Antibody Designed To Attack Tumour Cells".

J. Stephen etal, Biochem. J. (1966) 101,717 "Separation of Antigens by Immunological Specificity".

(List continued on next page.)

*Primary Examiner*—Kay A. Kim
*Attorney, Agent, or Firm*—Nixon & Vanderhye

[57] ABSTRACT

Synthetic antibody derivatives having at least two F regions covalently linked so as to enhance Fc activity for example effector recruitment. The use of such derivatives in the treatment of conditions where killing of cells is required for example cancer therapy. Methods for the preparation of derivatives are also described.

22 Claims, 10 Drawing Sheets

OTHER PUBLICATIONS

L. Riechmann et al. Nature, vol. 332, Mar. 24, 1988 "Reshaping Human Antibodies for Therapy".

Van Dijk et al. (1989) Int. J. Cancer 44 738–743.

Liu et al (1985) Proc. Natl. Acad. Sci. 82: 8648–8652.

Stevenson et al. (1989) Anti–Cancer Drug Design 3:219–230.

*Dictionary of Immunology* eds. Herbert, WJ. et al Third edition, Blackwell Scientific Publications Boston, 1985 pp. 79 and 108.

*Immunology* Eisen, Harper & Row, Publishers Hagerstown, MD 1974 pp. 409–410.

Hermentin et al (1988) Behring Inst. Mitt. 82:197–215.

Harris et al. (1993) TIBTECH II: 42–44.

Osband et al (1990) Immunology Today 11(6): 193–195.

Waldmann (1991) Science 252: 1657–1662.

Gould et al. (1989) J. Natl. Cancer Inst. 81(10): 775–781.

*Microbiology*, 2nd edition Reprint as *Immunology* Davis et al, 1974, Harper & Row, Publishers Inc. pp. 416–418.

Homologous linkage

Non-homologous linkage

Closed-hinge Fc

Open-hinge Fc

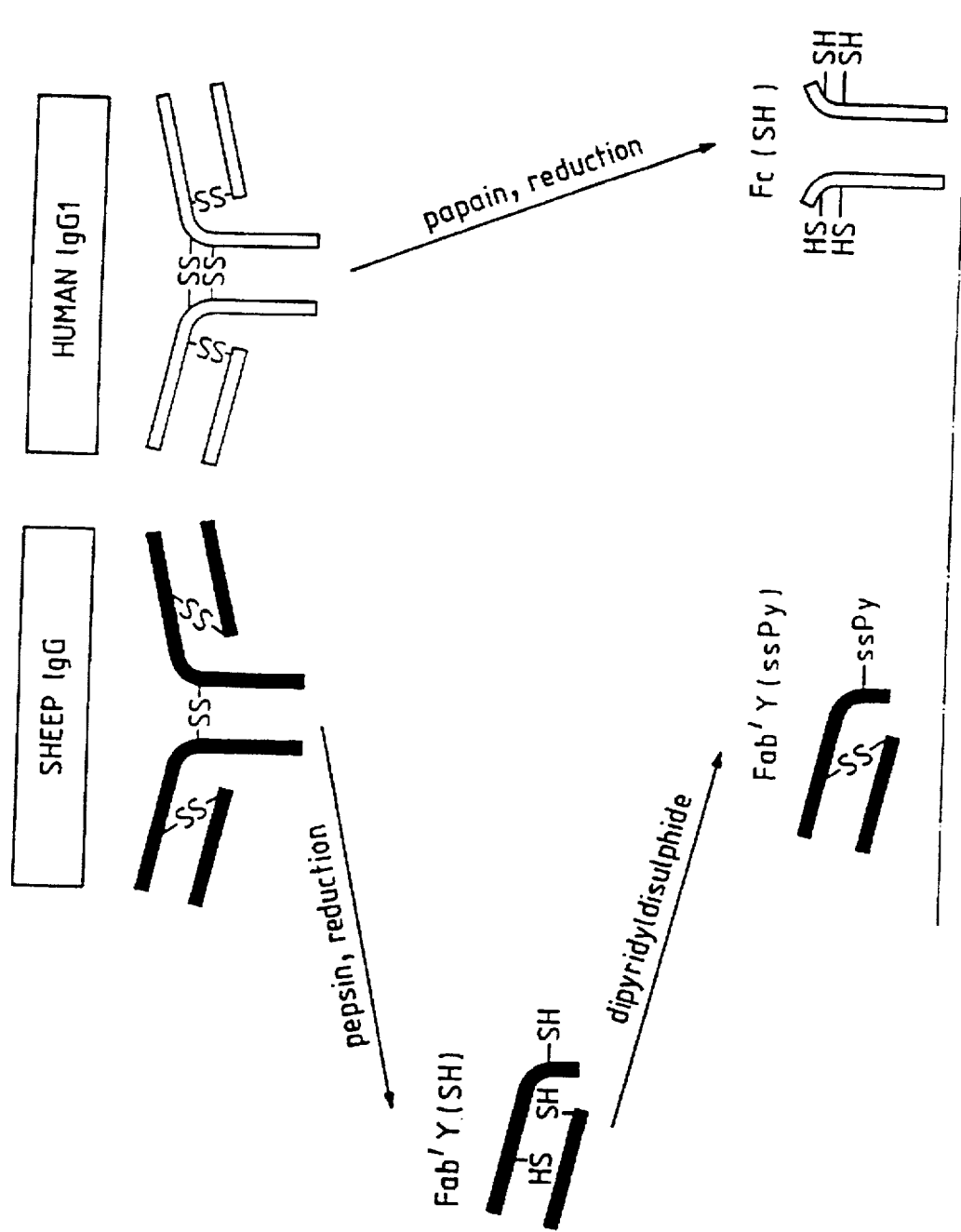

ANTIBODY CONJUGATES WITH TWO OR MORE COVALENTLY LINKED FC REGIONS

This is a continuation of application Ser. No. 07/678,950, filed as PCT/GB89/01269 Oct. 23, 1989, now abandoned.

This invention relates to antibody derivatives having multiple Fc regions and intended to have improved utility where enhanced Fc activity is required for example in human cancer therapy or in the treatment of other conditions where the killing of mammalian cells is desirable.

Monoclonal antibody technology has made available large numbers of antibodies with specificities directed towards differentiation antigens on tumours. Among B-lymphocytic tumours—lymphomas and leukaemias—a variety of antigens typical of various stages of B-cell differentiation have been revealed. These supplement the well studied idiotype (Id) on surface immunoglobulin (Ig), a set of epitopes whose collective specificity can be regarded as essentially unique for individual tumours.

Unless the context requires otherwise, the terms "antibody" and "immunoglobulin" are hereinafter used synonymously.

It is evident that the use of antibody to ablate a neoplasm would be an acceptable means of therapy if any normal antigen-bearing tissue damaged simultaneously could either be regenerated from antigen-negative precursors or safely dispensed with altogether. By such a criterion the surface Id and a number of the other B-lymphocytic differentiation antigens are promising targets for antibody therapy. The major problem is that antibody, having apparently evolved to deal with microorganisms, is simply not a good killer of mammalian cells. Thus, to date the majority of patients with B-lymphocytic neoplasms who have been treated with anti-Id have shown only a partial and transient diminution in tumour load. Among the factors apparently enabling the target cells to escape are inadequate recruitment of effectors by the antibody, antigenic modulation, mutations-affecting surface Id, and the development by the patient of an anti-antibody immune response.

One approach to rendering antibodies cytotoxically more effective has been the construction of chimeric derivatives, displaying antibody sites derived from xenogeneic antibody (usually mouse monoclonal IgG) and Fc regions derived from normal human IgG. The preparation of chimeric antibodies in which the antigen binding (Fab) arms of rodent IgG antibody are linked by thioether bonds to human IgG, or to the Fc gamma portion of human IgG, has been previously reported. Such a chimera has been prepared in quantity from monoclonal anti-Id and used in the treatment of human lymphoma [Hamblin et al., Blood, 42, 495 (1987) ]. In this chemically derived chimera the advantages expected from displaying human instead of rodent Fc gamma are better recruitment of effectors (complement and various cells displaying Fc gamma receptors), a longer metabolic survival and a lower immunogenicity. A comprehensive review of work in this field is contained in Cancer Surveys Vol.4 No.1 (1985) (Stevenson and Glennie).

Recruitment of at least two important effector mechanisms to antibody-coated cells relies on interactions with modest intrinsic association constants, reinforced simply by multiple binding. The interaction between Clq heads and C-gamma-2, which initiates the classic complement pathway, has a $K_A$ estimated at only 1.8 to $5.8 \times 10^4 M^{-1}$. To provide both firm binding and a conformational-signal to the Clq, simultaneous engagement of two or more heads with neighbouring IgG molecules on the target cells is required. The interaction between the Fc-gamma-receptor type III (FcRIII) and Fc-gamma, necessary for the antibody-dependent cellular cytotoxicity (ADCC) effected by large granular lymphocytes, has a $K_A$ of approximately $1.1 \times 10^7 M^{-1}$. The receptors are occupied efficiently only by entities capable of simultaneous multiple binding: thus lymphocytic ADCC can be inhibited by aggregated but not by monomeric IgG.

One object of the present invention is to provide antibody derivatives having improved Fc activity for example in regard to effector recruitment. Such derivatives are likely to have utility in the treatment of a range of conditions requiring the killing of mammalian cells for example in human cancer therapy, or in other conditions where enhancement of Fc function is beneficial.

According to the present invention there is provided a synthetic antibody derivative which comprises at least two Fc regions (as hereinafter defined) joined by covalent linkage and in which the number of any Fab regions (as hereinafter defined) present does not exceed the number of Fc regions.

Preferably the covalent linkage includes at least one synthetic chemical linking group.

Whilst the present invention should not be construed so as to include known natural structures, nonetheless, a range of structural forms may be obtained using the concept of the invention and a variety of preparative techniques may be employed in their manufacture.

Thus, the term "Fc region" as used herein and in the appended claims is intended to include not only, for example, typical immunoglobulin Fc structures comprising two peptide chains but also partial structures, active fragments and the like retaining Fc activity, e.g. recruitment effector ability or involvement in Ig transport and metabolism.

Fc regions may be derived from immunoglobulin of any class or species but if intended for human use are preferably from human immunoglobulin, e.g. IgG or IgGl. Polyclonal or monoclonal sources may be used.

The term "synthetic" is intended to distinguish from naturally occurring structures such as IgM but should not otherwise be construed in a narrow sense.

The covalent linkage between Fc regions is preferably synthetic in character, but should not necessarily be construed so as to exclude naturally occurring types of bond which may have been broken and reformed or the possibility for example of forming certain structures by techniques of genetic engineering using recombinant DNA.

According to one aspect of the invention the covalent linkage includes a synthetic chemical linking group. The linkage may be direct, which term includes linkages containing a synthetic linking group, or indirect, by which is meant a link including an intervening moiety, e.g. one having antibody-type activity, such as an Fab region.

The antibody derivatives of the invention will usually have at least one Fab region but the inventive concept is not necessarily limited in this way. Multiple Fc regions may, for example, be useful per se as starting material for construction of more complex structures.

In any event the choice of Fab region is not fundamental to the inventive concept and may be made from any immunoglobulin which provides the desired specificity for target cells. The possibility is also envisaged of replacing complete Fab regions having typical structures comprising two peptide chains, with partial structures, active fragments and the like or alternative moieties having the desired antigen binding or receptor properties. For example, a lectin which specifically recognises carbohydrate moieties on a target cell may be used.

In general, therefore, the term Fab region as used herein and in the appended claims should be understood to include any entity having specifity for a target cell and any moiety having functional properties similar to an Fab region.

Fab regions are preferably derived from monoclonal antibodies although suitable polyclonals may also be used.

Suitable monoclonal antibodies include those reactive against human cells and which are of mouse isotype IgG1 or IgG2a. They should preferably be readily digested for example with pepsin, to yield fragments which on reduction generate Fab gamma fragments containing the required sulphydryl groups.

In general herein, where Fc regions, Fab regions or synthetic chemical linking groups occur more than once in a structure or process it should be understood that they may be the same or different unless considerations of manufacture or use indicate otherwise.

According to further aspects of the present invention we provide:

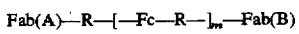

where,

Fab(A) is an Fab region from a first antibody A;

R represents a synthetic chemical linking group;

Fc represents an Fc region;

m is an integer greater than 1; and

Fab (B) is an optionally present Fab region from an antibody B which may be the same as, or different from A and which may be functionally under conditions of use.

When Fab(B) is absent the linking group may for example be alkylated instead.

However, although the present invention provides the possibility of producing, in general, synthetic antibodies which have multiple Fc regions, a preferred antibody of the invention comprises two Fc regions derived from human Immunoglobulin G (IgG), most preferably IgG1.

In the above formula R preferably represents in each case a linking group linked via a thioether linkage to a cysteine residue in an Fab region or in an Fc region at one end and to a cysteine residue in an Fc region at the other end of the linking group. For reasons which appear below R is often the residue of a divalent linker molecule. However, in some cases it may be preferred that R shall be the residue of a trivalent linker molecule. It is alternatively possible for R, particularly in an —Fc—R—Fc— moiety, to represent a group of the formula:

—R'—X—R'— where each R' represents a divalent linking group; and X represents a relatively bulky spacer molecule such as a protein or a peptide, for example plasma albumin.

An Fab region may contain up to about 11 cysteine residues in the hinge region. A typical Fab region has 3 cysteine residues in the hinge region. In the synthetic antibody of the invention two of these cysteine residues on an Fab region may be linked intramolecularly by a divalent group R whilst the third is linked by a divalent group R to an adjacent Fc region. If an Fab region is used that has only a single cysteine residue in the hinge region then again a divalent group R can be used to link the Fab region to an adjacent Fc region. However, if the Fab region has two cysteine residues only in the hinge region (e.g. an Fab region from mouse IgG3), then it may be expedient to use a trivalent group R to link the Fab region to an adjacent Fc region; in this case two of the valencies of the trivalent group R link to the two cysteine residues in the hinge region of the Fab region and the third to a cysteine residue on the Fc region.

The Fc regions are preferably linked one to another by a divalent group R. This can be the residue of a divalent linker molecule or it may be a group of the formula:

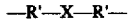

set out above.

A further representation of a synthetic antibody derivative, bisFabFc, of the invention is given in FIG. 1 herewith, in which S is a sulphur atom.

A preferred example of a divalent linking group R is a divalent residue of a bis-maleimide. An example of a trivalent linking group R is the residue of tris-(2-chloroethyl) amine.

In the group —R'—X—R'—, the divalent group R' may be, for example, bound at one end-by a thioether bond to a cysteine residue in the protein-X and at its other end by a thioether bond to, for example, a cysteine residue of an Fc region.

The synthetic antibody of this aspect of the invention may be univalent with only one of its Fab arms directed against the target cell and the other Fab arm being of irrelevant antibody specificity, i.e. being functionally inert as regards the target cell. Alternatively, the synthetic antibody of the invention may be bivalent with both Fab arms having the same activity; or it may be bispecific with each Fab arm directed against a different epitope on the target cell.

The present invention also provides a method of preparing a synthetic antibody comprising the steps of:

(a) selectively reducing isolated (Fab)$_2$ fragments of an antibody to form Fab fragments containing one or more free sulphydryl groups in the hinge region thereof;

(b) derivatising the Fab regions by introduction of the residue of a first synthetic chemical linking group reactive with free sulphydryl groups to form a derivatised Fab region which can still be reacted with sulphydryl groups;

(c) reacting the derivatised Fab regions with a molar excess of Fc regions recovered from the same or from a different antibody and having a sulphydryl group in the hinge region, thereby forming a product (FabFc) having one Fc region, one Fab region attached to one Fc chain and a free sulphydryl group at the hinge region of the other Fc chain;

(d) subjecting the FabFc product to thiol-disulphide interchange;

(e) derivatising the thiol-disulphide interchanged FabFc product by introduction of the residue of a second synthetic chemical linking group; and (f) linking the derivatised thiol-disulphide interchanged FabFc product with an FabFc product, prepared by the method of steps (a) to (d) above from the same or from a different antibody and having a sulphydryl group in the hinge region thereby to form bisFabFc in which the antigen binding arms Fab have the same or different specificities.

The separate Fab and Fc regions may be prepared by digestion of antibodies with pepsin or papain respectively and the selective reduction may be effected by treatment with dithiothreitol.

Derivatization may be effected by reaction of free sulphydryl groups with an at least difunctional linker molecule containing at least two functional groups capable of reacting with free sulphydryl groups. Examples of such functional groups include maleimido groups and chloro groups. Usually such a linker molecule contains two such functional groups; however, as explained above, it may be preferred to derivatise an Fab region with a trifunctional linker molecule, particularly when the Fab region has only two cysteine residues in the hinge region.

For the derivatization step (e) it is also envisaged that the thiol-disulphide interchanged FabFc product of step (e) may be linked to an inert protein, such as plasma albumin. If the inert protein does not already contain free sulphydryl groups these can be introduced by reaction with, for example, iminothiolane or 3-(2-pyridyldithio)propionic acid N-hydroxysuccinimide ester (SPDP). Linking of the sulphydryl groups on the inert protein with the thiol-disulphide exchanged FabFc product in step (e) can be effected by reaction with a cross linker molecule.

Step (f) can then be carried out by linking of the inert protein to the second FabFc moiety by reaction of a linker molecule with free sulphydryl groups on the inert protein residue and on the second FabFc moiety.

It will often be preferred to effect derivatization in steps (b) and (e) in each case by reaction with a linker molecule having the desired number of functional groups (usually two functional groups) capable of reacting with free sulphydryl groups.

A particularly preferred type of linker molecule is a dimaleimide of the formula:.

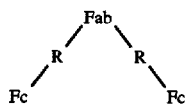

where R" is a divalent organic radical, for example an optionally substituted divalent aryl group or an optionally substituted divalent-aliphatic group. Such linker molecules include N,N'-o-phenylenedimaleimide and N,N'-bis(3-maleimidopropionyl)-2-hydroxy-1,3-propanediamine.

Other linker molecules which may be mentioned, particularly for linking certain types of Fab region to an adjacent Fc region, include tris-(2'-chloroethyl)amine.

The thiol-disulphide interchange may be effected by treatment with 2,2'-dipyridyldisulphide.

The sub-unit, FabFc, may under appropriate conditions, offer improvements over its parent antibody which are inherent in its chimerism: better effector recruitment, better metabolic survival and reduced immunogenicity. The sub-units may be prepared in high yield from any monoclonal antibody which can be digested to F(ab' gamma)₂ fragments, a group which includes the common mouse isotypes IgG1 and IgG2a. The Fab Fc derivatives may then be used as such or dimerized in any combination of available specificities to yield the bisFabFc of the invention. The following further possible improvements in performance may be expected:

(i) If the derivative remains functionally univalent, that is with only one Fab arm directed against the target cell, the number of Fc arms per cellular epitope is doubled and the Fc pairing offers co-operative binding of effectors.

(ii) If the derivative is bivalent, there is increased affinity for the target cell together with Fc pairing.

(iii) In bispecific bisFabFc an increased affinity results from the simultaneous binding of its two target epitopes. Escape of the target cell due to its being at the low end of a constitutive distribution of antigen, or due to a mutation affecting the antigen, will be more difficult because two antigens must comply with these criteria simultaneously. Inactivation of the antibody by extracellular antigen is rendered more difficult, provided only one of the target epitopes is secreted. The advantage of Fc pairing is, of course, also manifest.

According to an alternative aspect of the present invention antibody derivatives may be represented by the formula:

where;

Fc represents an Fc region;

R represents a synthetic chemical linking group;

Fab represents an Fab region;

n is an integer equal to or greater than 1; and where the Fc's may be further extended by additional (—R—Fc) groups.

Such derivatives may also be represented as:

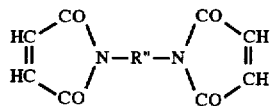

illustrating the indirect nature of the covalent linkage between the Fc groups which includes an Fab region.

The "parallel"-Fc geometry thus obtained offers the following potential advantages:

1. The parallel-Fc geometry is better suited to forming a regular array of Fc on the target cell for cooperative recruitment of effectors.

2. The preparation is simplified, and the yield of Fab in the final product improved.

3. The Fc hinges may be readily provided in either closed or open configuration (as defined below). In the latter form the derivatives will not activate complement, a feature which could prove advantageous when such activation is potentially toxic: in particular, when antibody is infused in the face of circulating soluble antigen.

By "closed" as used herein we mean that the peptide chains comprising the Fc region are linked by covalent bonding in or near the hinge region as illustrated in FIGS. 6A to 6C of the accompanying drawings and described in more detail hereinafter.

The covalent bonding may conveniently terminate in cysteine residues in either chain and consist of disulphide links or thioether links incorporating a suitable synthetic chemical linking group.

By "open" we mean, conversely, that no covalent bonding of this kind is present.

More detailed description of methods for the preparation of antibody derivatives according to the invention and of structures so produced are given in the examples provided hereinafter.

The antibody derivatives of the invention are likely to be useful in a range of applications where enhanced Fc activity is required. They may form the active principle in pharmaceutical preparations in conjunction with pharmaceutically acceptable diluents or carriers as appropriate to the type of treatment or mode of delivery.

Although the derivatives are likely to be useful against a range of targets including microorganisms they are likely to be especially useful where the killing of mammalian cells is required for example in the treatment of conditions where cells display antigens which may be recognised by Fab regions of the derivatives of the invention.

Such projected applications include use against cancerous conditions, cells infected with a virus or other intra-cellular microbe or rogue auto-immune cells such as abnormal lymphocytic clones causing auto-immune disease.

Further possible applications include purging of unwanted cells from bone marrow and immunosuppression of graft recipients.

Thus for example it is envisaged that synthetic antibody derivatives with multiple Fc regions could be extended to include structures of the type described in this application, but in which the Fab has been replaced by another moiety with a specific affinity for a surface molecule on the selected target cell. For example, a target cell infected with human immunodeficiency virus, and displaying on its surface the viral protein gp120, could be targetted by $(CD4)Fc_2$— a variant of $FabFc_2$ in which Fab has been replaced by the human normal protein for which the viral gp120 has a strong affinity. To make the product the CD4 would have to be provided with at least two sulphydryl groups near its C-terminus, by chemical or recombinant genetic means.

Derivatives provided by the present invention may therefore be useful in the treatment of AIDS.

Derivatives according to the invention may also have potential for targetting cells having Fc receptors in which case the Fab region would be used to bind the molecule which needs to reach the target, e.g. a toxin.

Derivatives may furthermore fund application in diagnostic tests and kits.

EXAMPLES

Examples of the invention will now be described with reference to the accompanying drawings in which:

ANTIBODY DERIVATIVES WITH DIRECT COVALENT LINKAGE

Figure 1:
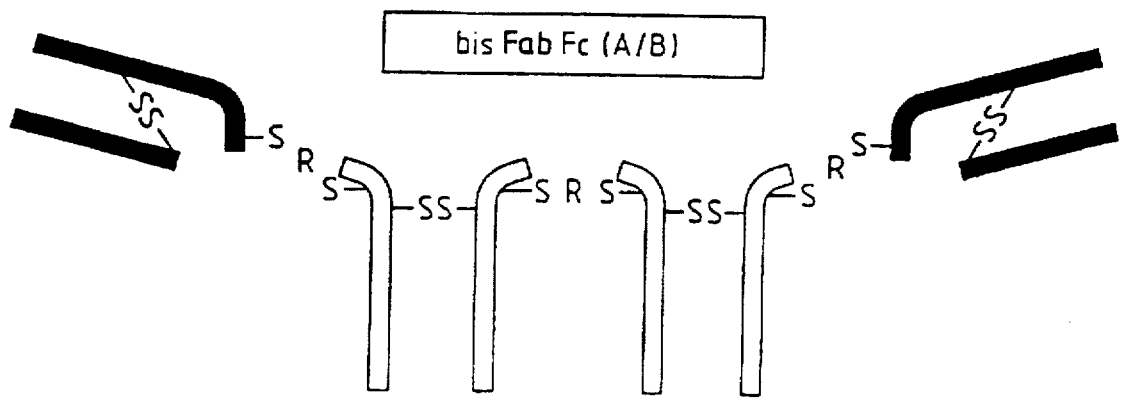
FIG. 1 is a diagrammatic representation of a synthetic antibody derivative having a direct covalent linkage between Fc regions.

Referring to FIG. 1 the unshaded portions represent two Fc regions directly covalently linked to each other by a synthetic chemical linking group R terminating in the sulphur atoms of cysteine residues forming part of the chains of the Fc regions. The Fc regions have a closed configuration, the individual chains of each being covalently linked via disulphide links formed from cysteine residues in the chains.

Each Fc region is further covalently linked via similar —S—R—S— linkage to an Fab region (shown shaded in the drawing) derived from monoclonal antibodies A and B which may be the same or different. The complete synthetic antibody derivative is referred to by the nomenclature bis-FabFc (A/B). Preparation and testing of derivatives as illustrated in FIG. 1 will now be described in more detail.

Materials

Dithiothreitol (DTT) from Sigma Chemical Company and 2-mercaptoethanol from British Drug Houses, were used without further purification. 2.2'-Dipyridyl disulphide (Py-SS-Py) from Aldrich Chemical Company was recrystallized from dimethylformamide (DMF)/water.

The bismaleimide crosslinkers, N,N'-o-phenylenedimaleimide (PDM) and N,N'-bis(3-maleimidopropionyl)-2-hydroxy-1,3-propanediamine (BMP) were each found upon titration to possess greater than 90% of the predicted maleimide activity and were used without further purification. Each was dissolved initially in DMF and, to minimise hydrolysis of the maleimide ring, diluted to the stated extent with aqueous buffer only immediately before use.

The affinity gel Protein A-Sepharose Cl-4B was obtained from Pharmacia. The cation-exchanger Phospho-Ultrogel A6R was obtained from Biotechnics (Villeneuve la Garenne, France).

Pepsin (from porcine gastric mucosa, product P6887, Sigma) was used without further purification. Papain was activated by incubation for 15 minutes at 37° C., pH 7.7 with 10 mM 2-mercaptoethanol, 5 mM EDTA. It was then passed at 20° C. through Sephadex G-50 (Pharmacia) equilibrated with 0.1M sodium acetate, pH 4.0, 1 mM EDTA, 5.5 mM 2-mercaptoethanol. The centre of the main protein peak was harvested and stored deep frozen in aliquots until required.

Preparation of FC Fragments

Human normal IgG was prepared from plasma surplus to blood bank requirements. A set of basic plasma proteins were first prepared by binding to the cation-exchanger SP-Trisacryl (IBF Biotechnics) in 40 mM Tris acetate, pH 6.0. After elution and buffer exchange they were led through DEAE-Sepharose FF (Pharmacia) in 50 mM Tris HCl, pH 8.0, and the unretarded IgG which emerged was harvested. This procedure yielded only the basic half of the IgG population, these molecules having the advantage that their Fab and Fc fragments were readily separable by ion-exchange chromatography.

To prepare the Fc gamma fragments the IgG (18 mg/ml) was digested at 37° C. for 30 minutes with papain (0.05 mg/ml) in the presence of 0.5 mM 2-mercaptoethanol at pH 6.6. Digestion was stopped by adding N-ethylmaleimide (22 mM in DMF) to 2 mM. The exposure to thiol entailed by these digestion conditions did not reduce any significant disulphide bonds in the IgG (less than 0.05/molecule by titration). The Fc gamma fragments were separated by sequential chromatography on Sephadex G-50, DEAE-Sepharose FF, and Sepharcryl S-200HR (all from Pharmacia). Passage through Sephadex G-50 separated IgG and its fragments from papain, and transferred them into 25 mM Tris HCl, pH 8.0, for ion exchange. On the DEAE-Sepharose column the Fc gamma and some of the undigested igG, but no Fab gamma, were retarded. The retarded material was eluted with 0.5M sodium chloride, 0.1M Tris HCl, pH 8.0 directly on to the Sephacryl for separation into IgG and Fc gamma. The Fc gamma fragments thus obtained were essentially entirely from IgG1: IgG2 is relatively resistant to cleavage under the digestion conditions used, IgG3 yields a large Fc gamma separated on the Sephacryl, and IgG4 is not present in significant amount in the basic IgG.

Preparation of Fab Fragments

Three mouse monoclonal antibodies were used. Anti-Id ($L_2C$), which is described in detail as anti-Id-1 by Elliott et al., Journal of Immunology, 138, 981 (1987) and by Stevenson et al. Br. J. Cancer (1984) 50, 407–413, is specific for the surface Ig idiotype on guinea pig $L_2C$ leukaemic cells. Samples are available from Dr. M. J. Glennie of the Lymphoma Research Unit, University of Southampton, Tenovus Research Laboratory, Southampton General Hospital, Tremona Road, Southampton, S09 4XY, UK. Anti-mu is specific for the heavy chains of human IgM and was raised in the laboratory and is available from Amersham International plc, Little Chalfont, HP7 9NA, UK. Anti-CD19, specific for the CD19 (p95) differentiation antigen on human B-lymphocytes, is secreted by the cell line RFB9 raised by, and available from, the Department of Immunology, Royal Free Hospital, Pond Street, London, NW3 2QG, UK.

F(ab' gamma)$_2$ from mouse IgG1 was prepared by limited digestion with papain. The progress of the digestion was monitored by chromatography of aliquots on Zorbax GF250 (DuPont). With IgG1 at 18 mg/ml, pepsin 0.3 mg/ml and pH 4.1, the digestion was usually close to completion within 8 hours at 37° C., with the adjustment of pH being critical. F(ab' gamma)2 was separated from the digest by recycling chromatography on Sephacryl S-200HR, equilibrated with 0.5M sodium chloride, 0.02M Tris HCl and pH 8.0.

Preparation of FabFC and bisFabFc

Figure 2A:
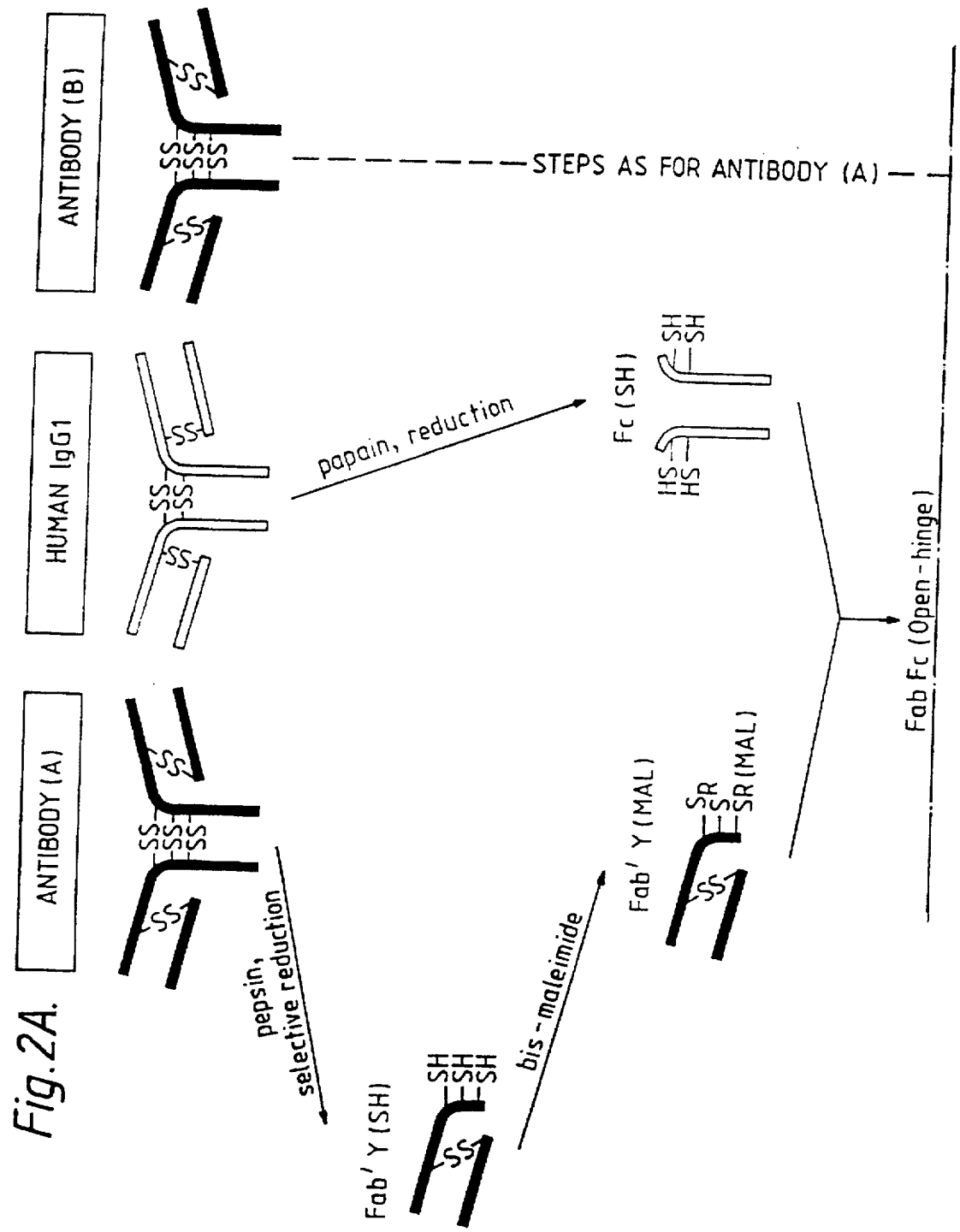
FIG. 2 illustrates a method for the preparation of the derivative of FIG. 1.
Figure 2B:
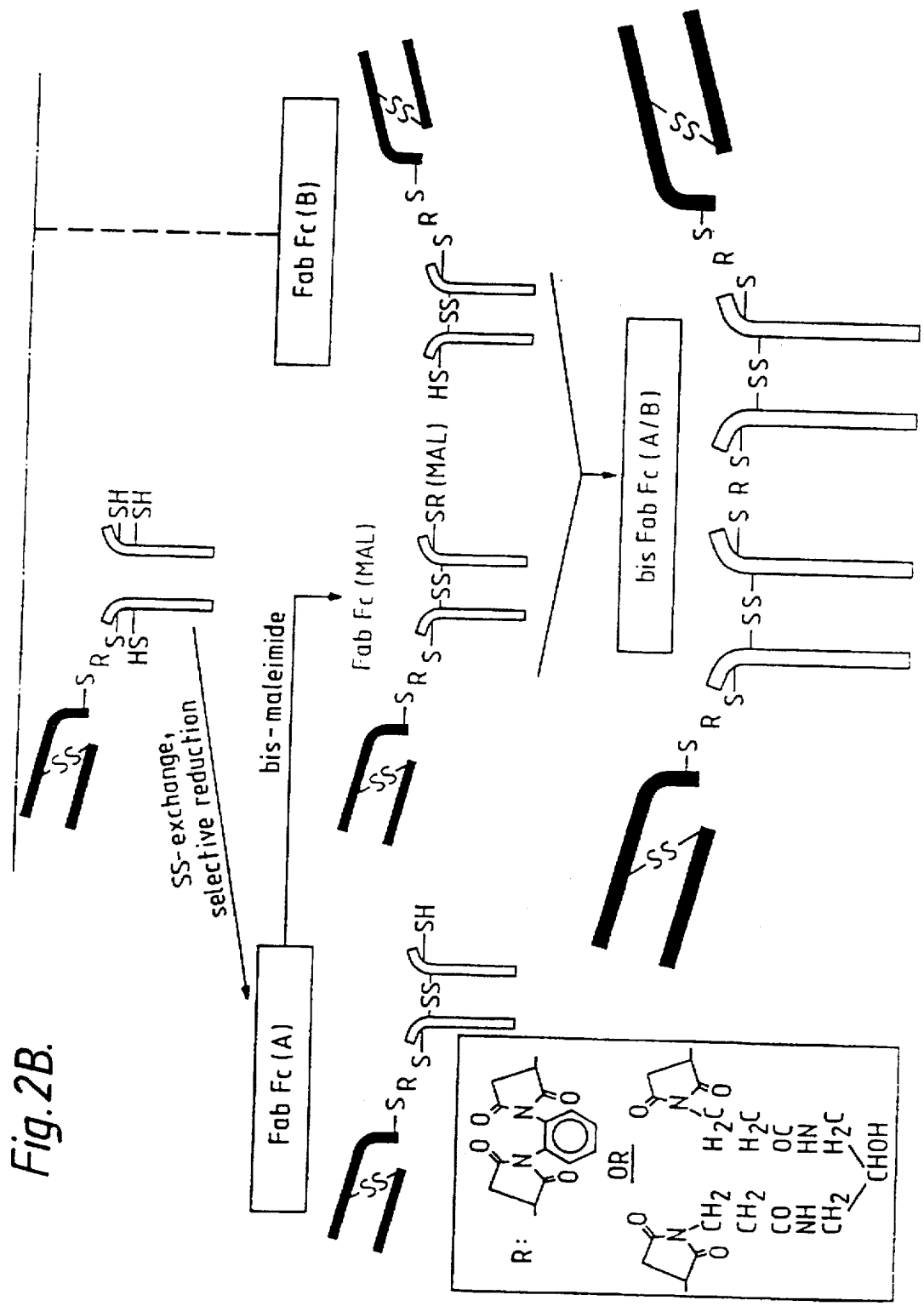

Reference is made to FIG. 2 herewith which summarises the steps involved in the preparation of FabFc and the bisFabFc.

F(ab' gamma)$_2$ from mouse IgG1 antibody is first reduced to yield Fab' gamma with free sulphydryl (SH) groups in its hinge region. These SH groups react with a surplus of bismaleimide linker (PDM) to yield a free maleimide group attached to the hinge. The Fab' gamma (mal) now reacts with reduced human Fc-gamma-1 containing free sulphydryl in its hinge, the Fc being in molar surplus to discourage combination with more than one Fab'. The resulting FabFc is separated by gel chromatography and binding to Protein A. To facilitate its effector functions the Fc hinge is closed by using thiol-disulphide interchange to re-form the disulphide (SS) bond whose contributing cysteine residues have not been involved in the thioether link to Fab'. This leaves a lone cysteine available for further reaction with a linker (PDM or the longer BMP) to yield FabFc(mal) for union with FabFc(SH). A variety of FabFc may be prepared, stored, used in this form, or, with further manipulation, dimerized by bisFabFc in any combination of specificities.

Selectively reduced Fab' gamma

The F(ab' gamma)$_2$ fragment obtained by peptic digestion of mouse IgG antibody was reduced with DTT at pH 8.0, allowed to undergo thiol-disulphide interchange with 2,2'-dipyridyldisulphide at pH 5.0 and again reduced with DTT at pH 5.0. After passage through Sephadex G-25 the resulting protein was found to have 2.9 titratable SH groups per kD, to migrate as 94% monomer, 6% dimer on gel filtration in Sephacryl S200 and to undergo little separation into its Fd' gamma and light chain constituents on SDS-PAGE. The predominant species (greater than 90%) was therefore monomeric Fab' gamma with its gamma-light SS bond intact, but with three SH groups derived from reduced inter-gamma chain bonds.

Derivatization of Fab'-gamma

After being passed through sephadex G-25 in 20 mM sodium acetate, 1 mM EDTA, pH 5.3, Fab'-gamma (SH) was allowed to react with 2 mM at this pH, at 5° C. for 30 minutes. DMF was present at 20% v/v. At the end of incubation one fifth volume of cold acetic acid was added, bringing the pH to 4.6. To remove the PDM and concentrate the protein, the solution was passed through Phospho-Ultrogel A6R, in 10%.DMF/90% Na$_2$EDTA, at 5° C. After rinsing, the Fab'-gamma(mal) was reverse-eluted with 0.5M sodium acetate, pH 5.3, and collected in an ice bath under nitrogen. Phospho-Ultrogel has the advantage of permitting compact elution at pH 5.3, so avoiding an increased rate of hydrolysis of maleimide groups at the higher pH values found necessary with other cation-exchangers.

Protein was collected at 4 to 8 mg/ml. Aliquots chromatographed on Sephacryl S-200HR revealed a dimer content of less than 5%, with higher aggregates usually not discernible. In four assays the maleimide content varied between 0.84 and 1.05 per molecule, sufficiently close to 1.0 in view of the approximations involved. No residual SH was detectable with Py-SS-pY. These findings imply that two of the hinge region SH groups have cyclized with the linker, leaving the third-to react with one end only. Such a result is very useful, as the presence of more than one maleimide group attached to the Fab' hinge will increase the tendency to form higher order aggregates when Fab' reacts with human Fc-gamma.

The longer linker BMP has the advantage of greater solubility than PDM, and a greater stability of its malemide groups due to their being alkyl- rather than aryl-linked. However, when used in the above protocol at 2 mM it gave a greater tendency to cross-link the Fab', giving a dimer content of greater than 15%. When its concentration was raised to 4 mM the amount of dimer formed was less but it then yielded 1.3 to 1.6 maleimide units per Fab', and was associated with greater formation of aggregates in the Fab'-Fc interaction than was seen using PDM. Both of these problems with BMP are explicable on the basis of its being less likely than PDM to cross-link intramolecularly two of the three available SH groups.

Formation of FabFc

Human Fc-gamma was reduced by reaction with 6 mM DTT, pH 8.0, for 15 minutes at 37° C., passed through Sephadex G-25 in 0.5M sodium acetate, pH 5.3, and collected in an ice bath under nitrogen. Titrated SH groups have been in the range 3.2 to 3.6 per molecule, to be compared with a theoretical 4.0. Examination on SDS-PAGE revealed no surviving protein in the 50 kD position, and hence no surviving hinge SS group. The relatively low titration suggest some proteolytic loss of hinge.

Immediately upon its being prepared Fab'-gamma(mal) was added to constantly stirring Fc(SH) at a molar ratio Fab:Fc of 1:2.5. The mixture, with a minimum protein concentration of 7 mg/ml, was incubated at room temperature for two hours. Any reduction in the molar excess of Fc increased the amount of aggregate which formed, the aggregate being interpreted as mainly greater than one Fab per Fc. Economically a waste of Fc is much less serious than a waste of the antibody Fab, and the excess Fc is not usually recovered.

FabFc was separated from aggregate and from surplus Fc by recycling chromatography on Sephacryl S200HR in 0.5M sodium acetate, 5 mM EDTA, pH-5.8, at 5° C. 2-mercaptoethanol was present at 2 mM to inhibit a small amount of oxidative dimerization of Fc which otherwise tended to occur. Typically the separated aggregate amounted to about 10% of the protein present in the FabFc (100 kD) peak. The FabFc was led from the Sephacryl on to a Protein A-Sepharose column to which it, but not any contaminating F(ab'gamma)$_2$, binds.

Thiol-disulphide interchange to close the Fc hinge was carried out at pH 5.3 while the FabFc remained bound to the Protein A column. After rinsing off the 2-mercaptoethanol a solution of 0.1 mM Py-SS-Py in 5% DMF was passed through the column at 5° C. for 30 minutes. There was a prompt release of 2-thiopryridone, which appeared at the front of the emerging Py-SS-Py. The amount released, when related to the amount of protein subsequently eluted, indicated a reaction with 2.3 to 2.8 SH groups per FabFc (theoretical 3.0).

At this stage, with its unlinked hinge cysteine present as a 2-pyridyldisulphide, the FabFc may be eluted for immediate use or for a subsequent incorporation into bisFabFc. If it is proposed to proceed at once to bisFabFc, the protein may be left on the column for further manipulation.

The recovery of Fab' in FabFc, in terms of F(ab'-gamma)$_2$ used at the outset, is about 65%.

Formation of bisFabFc

Two lots of FabFc, of the same or different antibody specificities, were isolated on separate Protein A columns. On one the unlinked cysteine was returned to the SH form, on the other it was given a maleimide group by reaction with a bismaleimide linker. The linker was usually BMP, chosen because its long alkyl chain should permit greater separation of the two Fc than would PDM, thereby facilitating the simultaneous binding of effector molecules to each Fc. However, a comparison of the two linkers in the inter-Fc position failed to demonstrate any clear advantage in effector recruitment. Therefore, BMP was generally used because of its greater solubility. Amounts of FabFc were adjusted to give a molar ratio of FabFc(SH):FabFc(mal) of 1:1.1, to allow for some attrition of the maleimide.

In detail, FabFc on both Protein A columns had their unlinked hinge cysteine (present as a 2-pyridyldisulphide) selectively reduced by passage of 0.7 mM DTT, pH 5.3, through the columns at 5° C. for 30 minutes. The effluent DTT was accompanied by 2-thiopyridone, 0.80 to 0.92 molecule per FabFc. This figure confirms that the earlier reaction with Py-SS-Py must have largely re-established the SS bond between the paired cysteines in the Fc hinge. To prepare FabFc(mal) one of the preparations was allowed to react with 8 mM BMP in 12.5% DMF, 20 mM sodium acetate, pH 5.3, passed through the column at 5° C. for 30 minutes.

After washing surplus reagents from the columns, FabFc (SH) and FabFc(mal) were eluted in the one solution by passing 0.1M glycine hydrochloride through the columns in tandem. The pH was adjusted to 5.5 with sodium acetate and the solution incubated at 20° C. for 16 hours. The elution volume was kept to a minimum by attention to column geometry: a protein concentration of greater than 10 mg/ml is desirable because the formation of thioether bonds competes with hydrolysis of maleimide.

At the end of the incubation period, chromatography of aliquots on Sephacryl S200 revealed that up to 77% of the protein migrated as a 200 kD species. Apart from a minute amount of higher aggregate, the remainder behaved as 100 kD species. Examination on Ouchterlony plates revealed that the 200 kD species contained mouse Fab and human Fc epitopes on the one molecule, and revealed no molecules containing epitopes of only one type. This fraction is therefore regarded as essentially entirely bisFabFc. The 100 kD fraction contained molecules with both the Fab and Fc epitopes, i.e. FabFc, as its principal constituent, but there was a small amount of putative Fc$_2$.

The entire preparation may be separated chromatographically into its bisFabFc and FabFc components if so desired. However, for therapeutic use there is no need to do so as a small amount of FabFc is not obviously disadvantageous. Additional steps required for therapeutic preparations are the removal of pyrogens, by meticulous exclusion throughout or by partial exclusion followed by chromatography on a polymyxin column; and passage through a bacterial filter (0.22 micrometers) immediately before collection into a sterile container.

Effector Functions of bisFabFc

Three preparations with the following specifications were examined: (a) anti-Id/anti-Id, with both arms directed against surface Id on guinea-pig L$_2$C cells; (b) anti-Id/0 with one anti-Id (L$_2$C) and one irrelevant arm (from an IgG1 anti-Id raised against a human tumour), effectively univalent for L$_2$C cells; (c) anti-mu/anti-CD19, directed against the indicated antigens on human lymphoid cells. Preparations (a) and (b) were tested against L$_2$C cells, preparation (c) against the human B-lymphoblastoid line Daudi. None of the parent mouse IgG1 antibodies showed any activity whatever in assays of complement lysis or lymphocytic ADCC against these targets.

Figure 3:
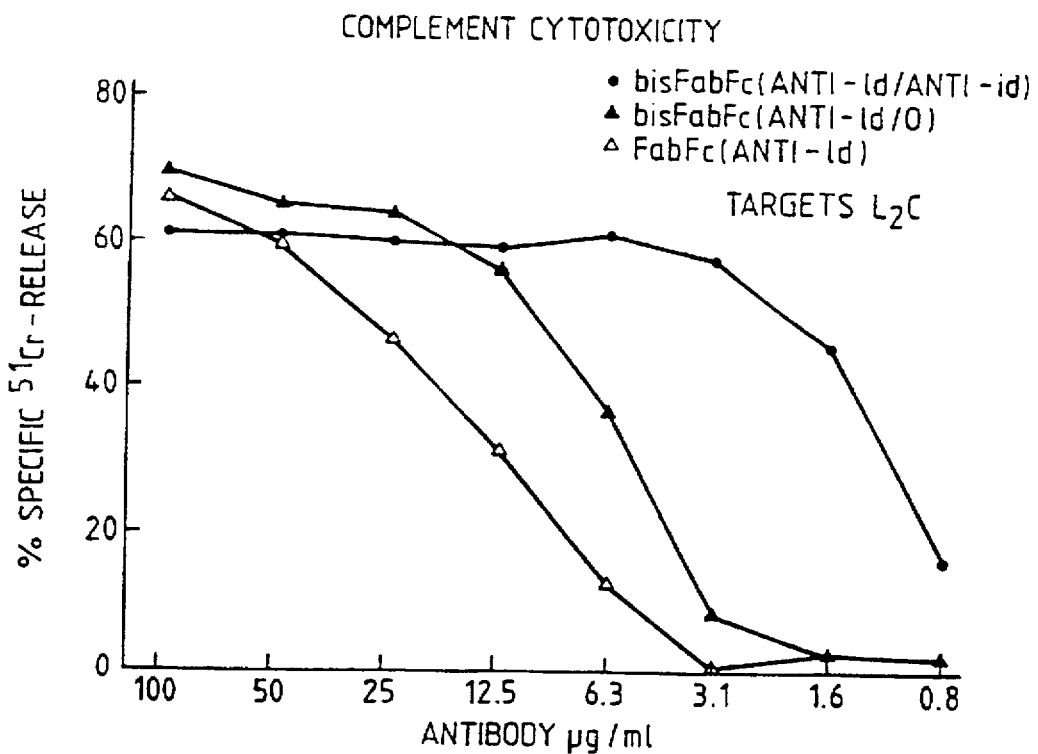
FIG. 3 is a graph of complement cytotoxity comparing derivatives according to the invention with another derivative.

FIG. 3 shows that for complement lysis bisFabFc (anti-Id/0) had about twice the titre of the parent FabFc when considered by weight, and about four times the titre as judged by molarity of active antibody sites. Two factors could have contributed to this superiority, the increased number of Fc on the cell and the juxtaposition of Fc in pairs. These factors cannot be separately evaluated at present.

BisFabFc (anti-Id/anti-Id) outperformed the univalent bis derivative whether charted by weight (FIG. 3) or by molarity of active antibody sites. A contribution to this improvement must have arisen from the increased affinity associated with bivalent binding, but a negative factor could have been a greater tendency for the bivalent derivative to induce antigenic modulations of the surface Ig [Gordon & Stevenson, Immunology, 42, 13 (1981)]. In fact flow cytofluorimetry did not reveal any modulation of L$_2$C cells induced by bisFabFc (anti-Id/anti-id) over a period of 30 minutes: this may relate to the long flexible inter-FabFc link, or to the fact that the parent IgG1 anti-Id is itself a poor modulator with a probable "monogamous" mode of binding to the surface Ig [Elliot et al, Journal of Immunology 138,981 (1987)].

Figure 4A:
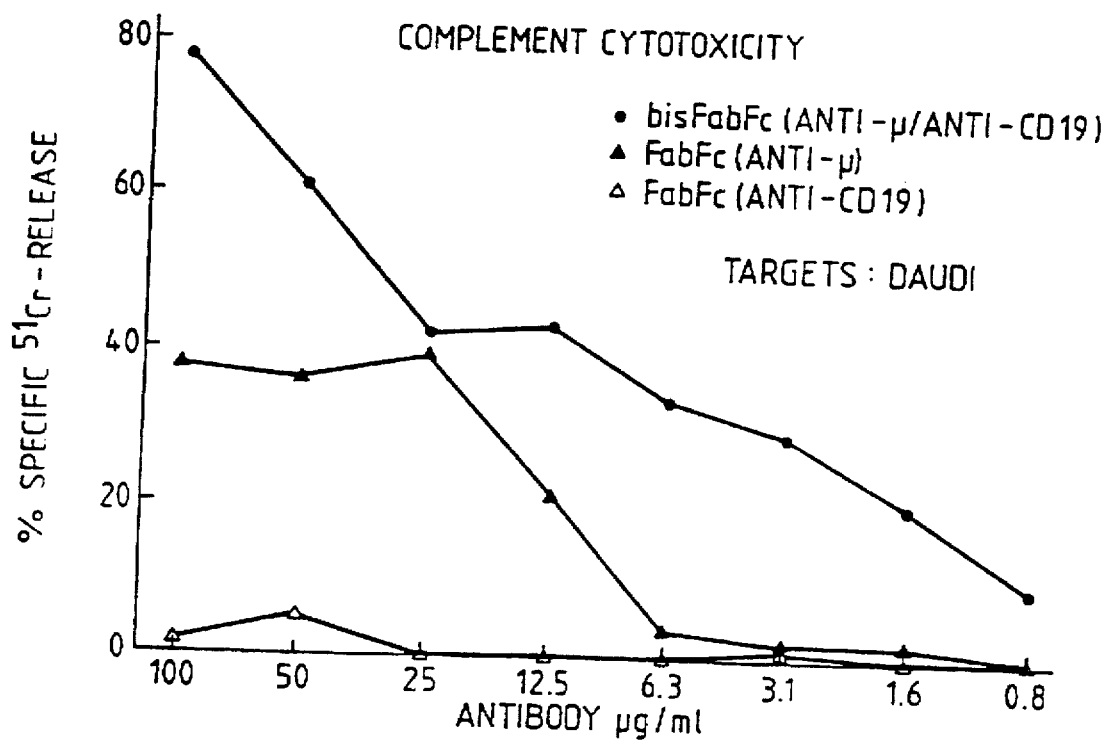
FIG. 4 shows graphs comparing the activity of a derivative according to the invention with other derivatives, 4A relating to complement cytotoxity and 4B to antibody-dependent cellular cytotoxicity (ADCC)
Figure 4B:
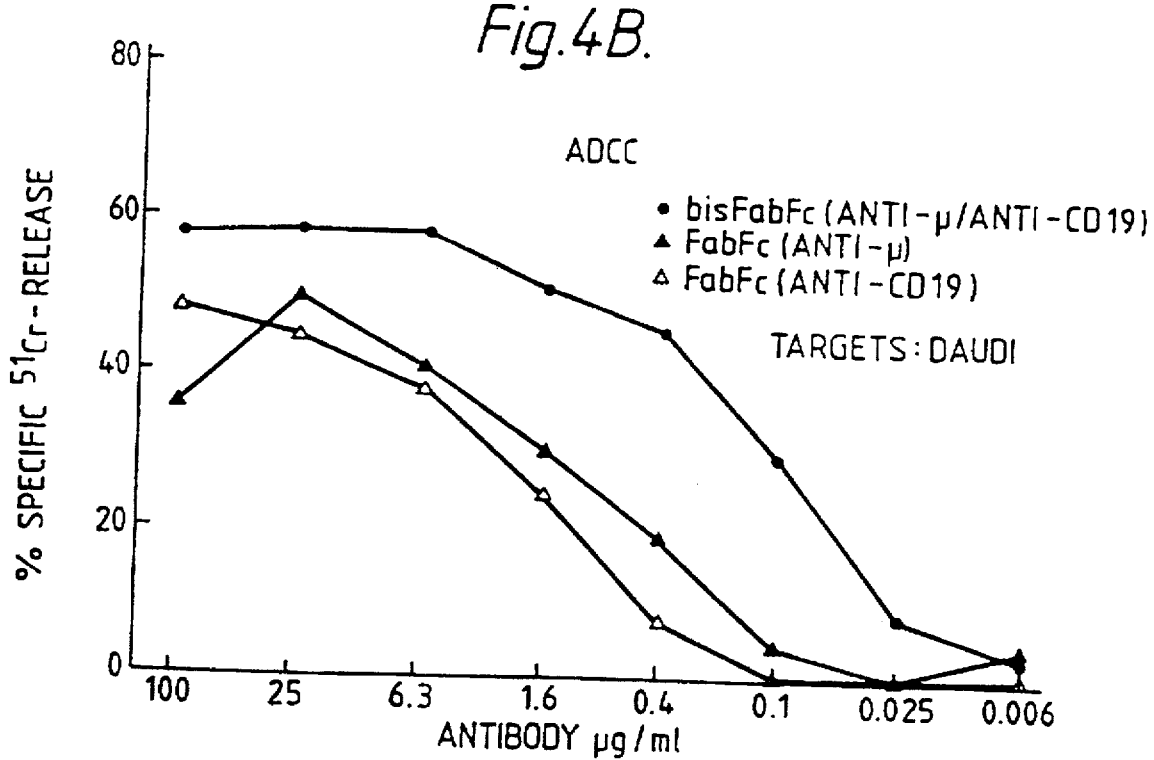

In FIG. 4 the performance of bisFabFc (anti-mu/anti-CD19) is compared with those of both parental FabFc. In ADCC the bis derivative revealed a titre about 16 times that of either parent. The complement killing was poor overall but the superiority of the bis derivative is clear. Again these simple assessments do not permit the contributions of multiple factors—binding affinity, Fc per cell, juxtaposition of Fc, and possible incipient modulation—to be disentangled.

On no occasion have assays of complement lysis revealed a prozone which would suggest anti-complementary activity of bisFabFc.

Antibody-invoked Cytotoxicity

Complement-mediated killing of $^{51}$Cr-labelled, antibody-coated cells was carried out by standard methods. The complement source was fresh serum from normal rabbit or guinea pig, at a final dilution of 1:5. ADCC was carried out using freshly isolated lymphocytic effectors from normal human blood, at an effector:target cell ratio of 50:1. Human AB serum (inactivated) was present at 10%. The extent of lysis was read at 3.5 hours.

Percentage cytotoxicities represent the means of duplicates, calculated in the standard manner, that is:

| counts released with antibody | counts released with normal IgG. |
|---|---|
| counts released with detergent | counts released with normal IgG. |

Antibody derivatives with indirect covalent linkage

Figure 5:
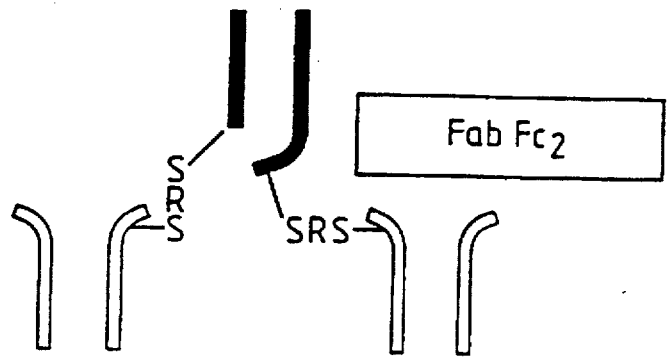
FIG. 5 is a diagrammatic representation of a synthetic antibody having an indirect covalent linkage between Fc regions.
Figure 6A:
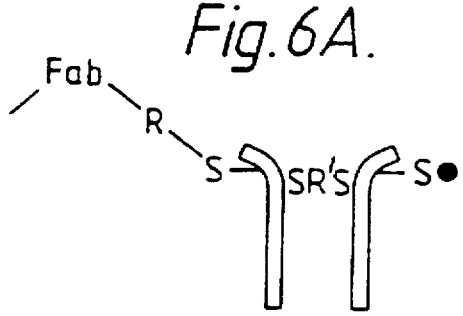
FIGS. 6A–6D show details of open and closed configurations for Fc regions.
Figure 6B:
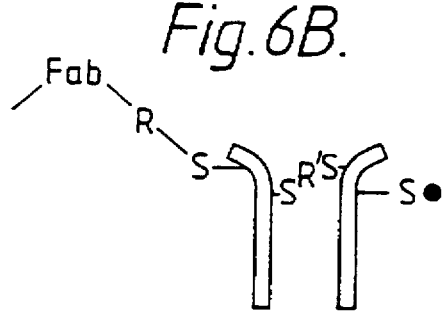
Figure 6C:
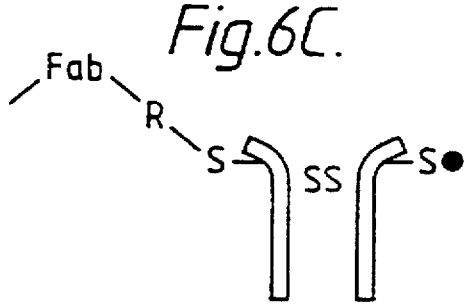
Figure 6D:
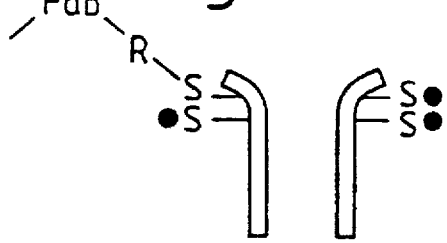

Referring now to FIG. 5 of the drawings the unshaded portions represent two Fc regions indirectly linked to each other via a covalent linkage which includes an intervening Fab region (shaded). Links between regions involve synthetic chemical linking groups R terminating in sulphur atoms of cysteine residues in the individual chains of the regions. As shown, both chains of the Fab regions are linked to an Fc region but it will be appreciated that, provided enough reactive groups are present, both Fc regions could be linked to one chain. The complete derivative is referred to by the nomenclature Fab Fc$_2$.

More details of Fc regions with closed or open configurations are shown in FIG. 6 in which 6A–6C are closed and 6D is open.

The hinge in FabFc$_2$ (closed) is closed by reconstruction of one of its disulphide bonds, or by tandem thioether bonds separated by the group R', in homologous (FIG. 6A) or non-homologous (FIG. 6B) linkage.

S● indicates a thiol group rendered inert by alkylation or other means.

A random element in the chemical synthesis means that possibly any two of the five indicated S atoms on Fab can participate in the linkages to Fc; and in turn that any one of the four S atoms in the Fc hinge can be involved in a linkage to Fab. (See the fuller structural formulae in FIG. 9).

Details of methods for the preparation of antibody derivatives of the type illustrated in FIG. 5 now follow.

Principles

Figure 9A:
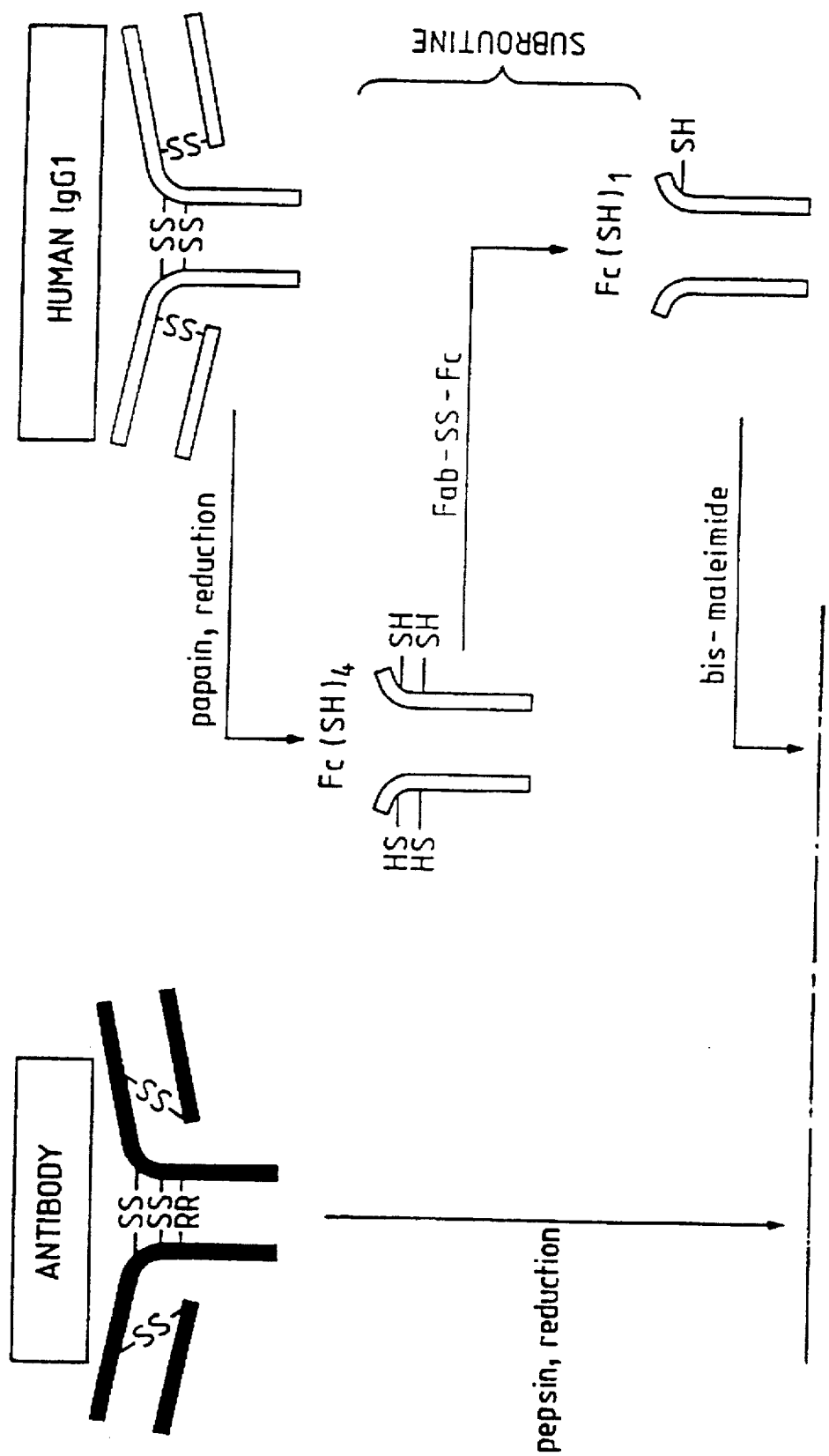
FIG. 9 illustrates a method for the preparation of the derivative of FIG. 5.
Figure 9B:
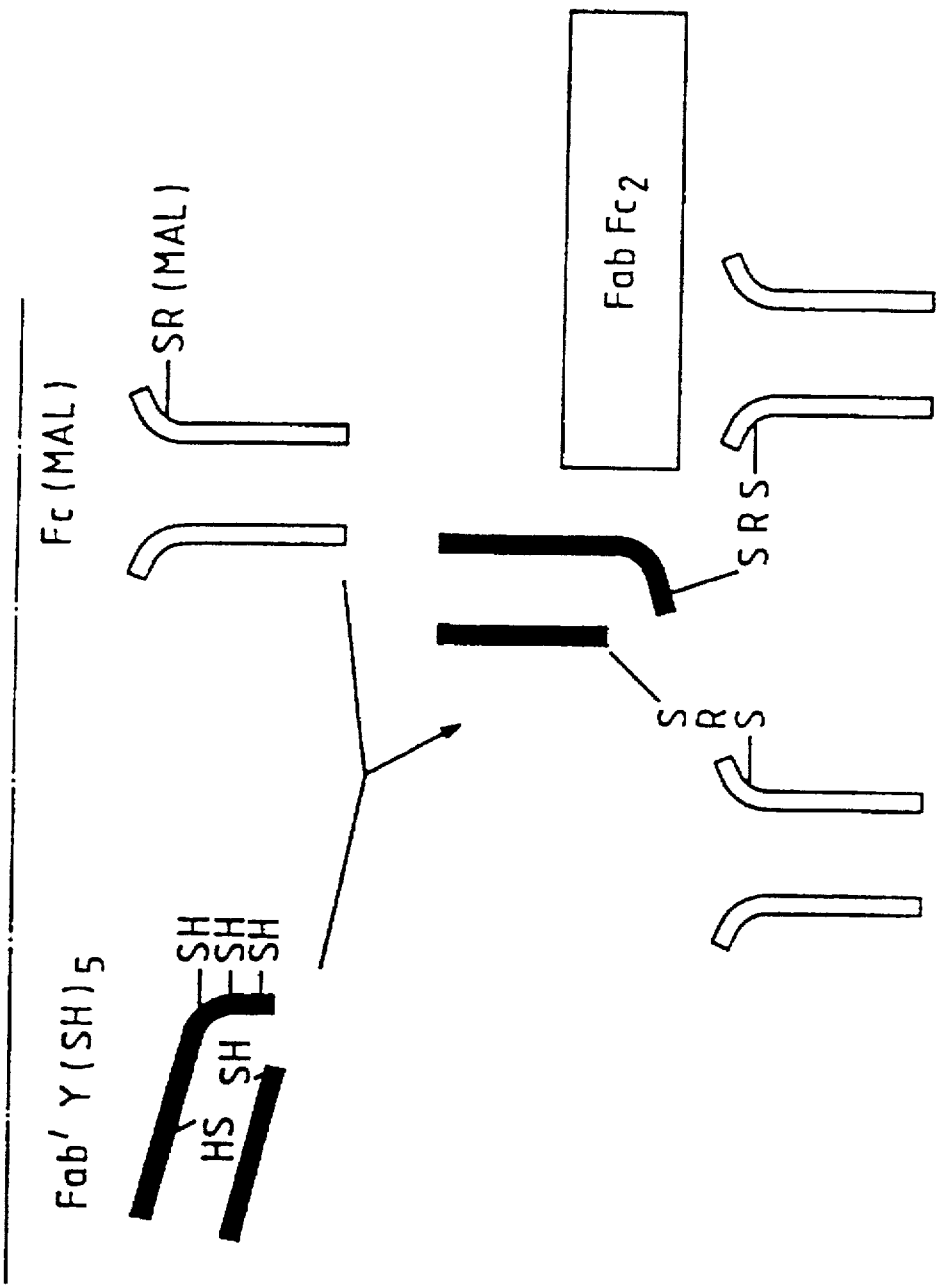

1. The basic preparative step involves the reaction of Fc gamma having a single maleimide group in its hinge, Fc (mal), with Fab which has free SH groups (FIG. 9). The SH groups in Fab arise from reduction of all its interchain disulphide bonds, and in the majority of cases (Fab' derived from mouse monoclonal IgG1 or IgG2a) such Fab will have five SH groups: Fab (SH)$_5$. In other cases the number of groups could vary from three (e.g. from mouse IgG3) to six (e.g. from mouse IgG2b), but such variation will entail no more than minor amendments to our preparative procedure.

2. It is found that the reaction of Fc(mal) with Fab(SH)$_5$, in a molar ratio of Fc:Fab$\geq$3, yields FabFc$_2$ as its major product (FIG. 9).

3. The minor products are FabFc$_3$ and FabFc: these can be removed, but present indications are that no harm accrues from leaving them with the FabFc$_2$ in order to improve the yield of product.

4. The reason for FabFc$_2$ being the major product, even when the reaction mixture contains a molar ratio of Fc:Fab$\geq$3, is that steric hindrance discourages further access of Fc(mal) to SH groups after the formation of FabFc$_2$.

5. The preparation of Fc(mal) entails a subroutine which leaves the Fc gamma as an intermediate product Fab-SS-Fc (sacrificial FabFc) for storage. The Fab moiety (at present sheep Fab' gamma) is discarded, although some recycling is possible. The subroutine makes Fc available in a univalent combining form: this simplifies the products of the final (Fab+Fc) reaction, preventing in particular the formation of species with more than one Fab.

6. In sacrificial FabFc the sheep Fab' gamma blocks a single cysteine residue in the Fc hinge. This permits the substitution of a single maleimide group on the Fc in one of two ways.

a. Subroutine (1), used for the preparation of both Fc(mal) with open hinges and Fc(mal) with thioether-bonded hinges. The cysteine residue on which the sheep Fab' gamma is placed is that which eventually bears the maleimide group;

b. Subroutine (2), used for preparation of Fc(mal) with disulphide-bonded hinges. The cysteine residue which bears the maleimide group is directly opposite the residue bearing the sheep Fab' gamma.

Figure 7B:
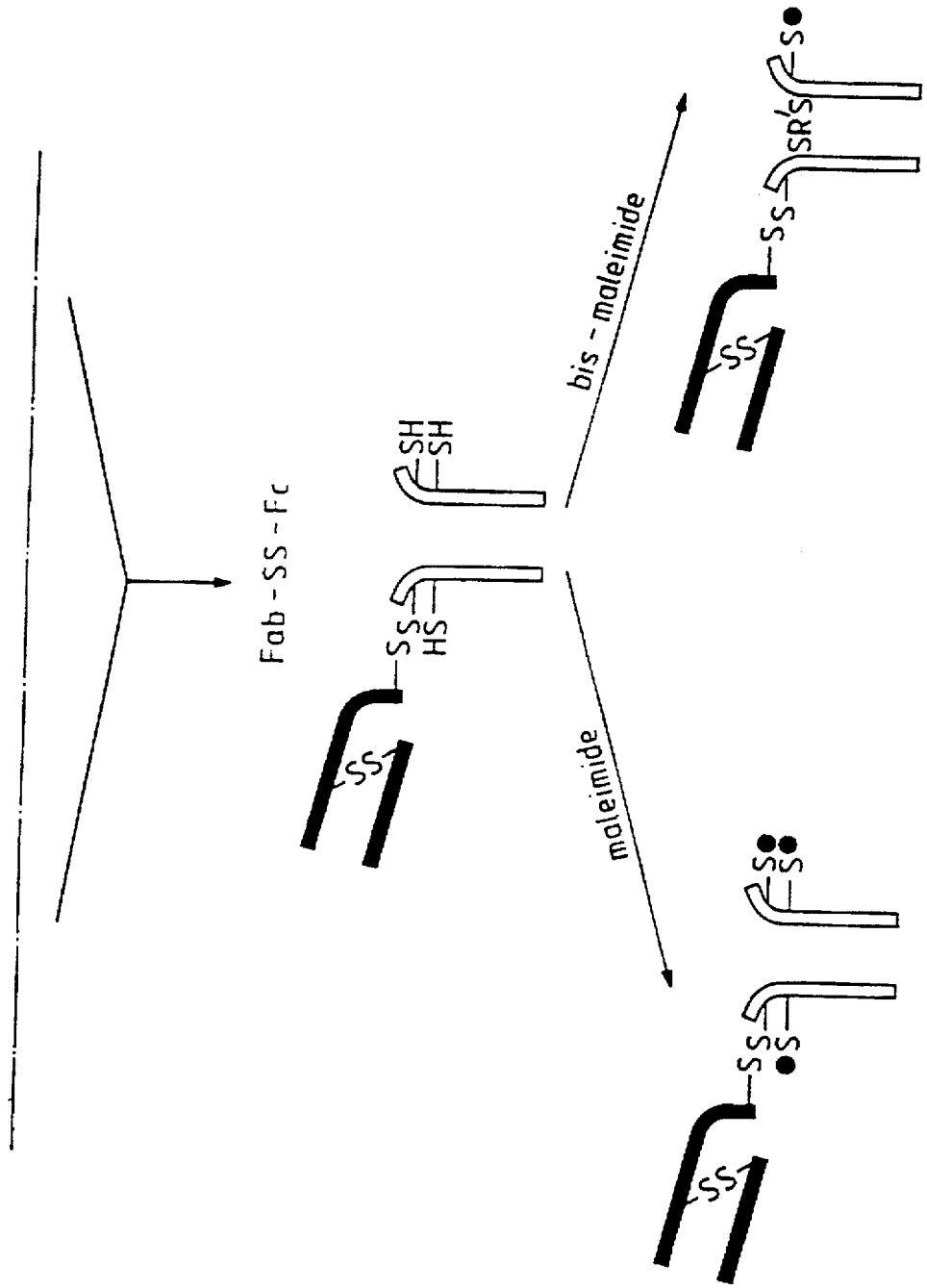
FIG. 7 illustrates a sub-routine used to produce an intermediate structure.

Subroutine (1) for sacrificial FabFc (FIG. 7)

1. The F(ab' gamma)$_2$ fragment obtained by peptic digestion of sheep normal polyclonal IgG is reduced with dithiothreitol (DTT) at pH 8.0 and allowed to undergo thiol-disulphide interchange with 4,4'-dipridyldisulphide at pH 5.0, as described previously for mouse Fab' gamma (Principles para 1). The product (Fab-SS-Py) has a single mixed pyridyl disulphide at the site of the former inter-Fab disulphide bond.

2. The interchain disulphide bonds of human Fc gamma are reduced by reaction with DTT as described previously (Principles para 1).

3. Fab-SS-Py and Fc(SH)$_4$ are allowed to undergo disulphide interchange at 25° C. and pH 4.4, with Fab and Fc equimolar. At this pH pyridyldisulphides are uniquely susceptible to the nucleophilic attack by thiol which is entailed in disulphide interchange. In contrast the disulphide bond which is formed between Fab and Fc undergoes little degradation at the acid pH, despite the proximity of protein SH groups (FIG. 7), before the SH groups are rendered inert by alkylation. The disulphide-bonded products which form are FabFc (major) and Fab$_2$Fc (minor), with very little larger. With the total protein concentration at 5 mg/ml or greater, 30 minutes is sufficient for this reaction.

4. If the Fc hinge is required in open form, disulphide interchange is stopped by alkylation with N-ethylmaleimide at pH 5.0.

5. If the Fc hinge is required in closed form the alkylation is carried out with the bivalent linker o-phenylenedimaleimide (FIG. 7). The linker can bridge the three remaining SH groups in three ways, two of which result in the hinge being closed. Consistent with this reasoning the majority of Fab-SS-Fc molecules so alkylated are found by electrophoresis in a dissociating medium to have the halves of their Fc components covalently joined. The unbridged SH group will react with the linker to leave a free maleimide group, which can be inactivated by brief exposure to 2-mercaptoethanol at pH 5.0.

6. Sacrificial FabFc is separated from other reaction products and from residual reactants by gel chromatography on Sephacryl S200HR (Pharmacia).

7. The sacrificial FabFc is stored at 5° C. until required, and has proved stable under these conditions for at least three months.

Figure 8:
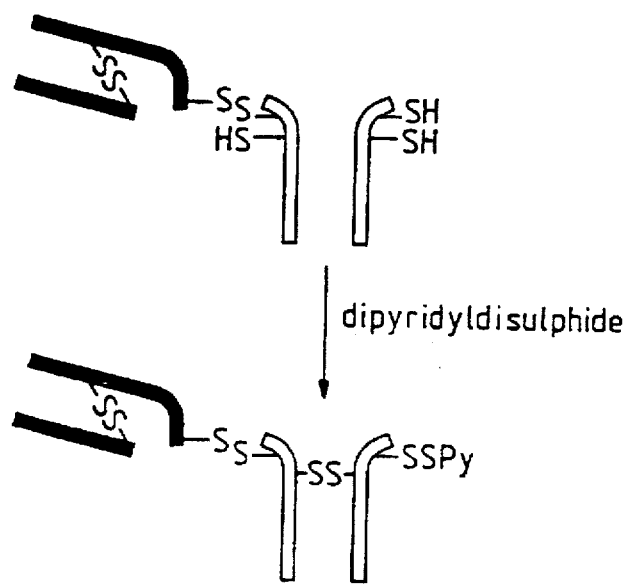
FIG. 8 illustrates a part of an alternative sub-routine.

Subroutine (2) for sacrificial FabFc (FIG. 8)

1. )
2. ) As for Subroutine (1) immediately above.
3. )

4. Dipyridyldisulphide is added to 0.2 mM and disulphide interchange allowed to proceed for a further 30 minutes at 25° C. As a result those hinge disulphides where both cysteine residues remain available are closed (see reference (1) for a discussion of the mechanism of closure of protein disulphide bonds by such interchange), and other residual cysteine residues are converted to the mixed disulphide protein-SS-Py.

5. Sacrificial FabFc, now in a stable form with the disulphide configuration Fab-SS-Fc-SS-Py (FIG. 8), is separated by gel chromatography on Sephacryl S200HR, and stored at 5° C. until required.

Main Reaction

The major features of the main reaction, joining mouse Fab' gamma to human Fc, are set out in FIG. 9. There are some differences in detail according to whether the sacrificial FabFc used comes from Subroutine (1) or Subroutine (2).

Referring to FIG. 9, only those bonds joining the mouse Fab' gamma and human Fc moieties are shown, so that the diagram suffices for all variants of FabFc$_2$: with open hinges, thioether-bonded hinges, and disulphide-bonded hinges. In the preparation of the last of these variants sheep Fab' gamma remains attached to the Fc, opposite the maleimide group, until after the Fc has been linked to antibody Fab' gamma A. Using Sacrificial FabFc from Subroutine (1)

1. F(ab' gamma)$_2$, derived from peptic digestion of mouse monoclonal IgG antibody, is reduced with 3 mM DTT at 25° C. and pH 8.0 to yield Fab(SH)$_5$. The pH is then lowered to 5.0 and the ionic strength to 0.02 or less (by addition of dilute acid, or by passage through Sephadex G-25 (Pharmacia) equilibrated with 0.02M acetate buffer of pH 5.0), permitting the protein to be led onto and bound to the cation-exchanger Phospho-Ultrogel 6B (I.B.F. Biotechnics).

2. Sacrificial FabFc is led onto a column of protein A-agarose, which has a high affinity for Fc gamma. A solution of 6 mM DTT in buffer at pH 8.0 is put through the column at 5° C., reducing the inter-subunit disulphide bond and releasing the sheep Fab' gamma in the column effluent. This Fab' gamma may be collected for re-use if desired.

3. Fc(SH) is now eluted from the column with 0.1M glycine-HCl, pH 3.0, and allowed to react with a bis-maleimide linker. Linkers which have been used are N,N'-o-phenylenedimaleimide at 2 mM and N,N'-bis(3-maleimidopropionyl)-2-hydroxy-1,3-propanediamine at 5 mM. The linkers are dissolved in dimethyl-formamide prior to being added to the protein solution. Final conditions for attachment of the linker are Fc 0.25 mM, linker at 2 or 5 mM, dimethylformamide up to 20% V/V, pH 5.3, 5° C. After 30 minutes the protein, now in the form of Fc(mal), is separated from the linker and transferred into 0.5M acetate buffer, pH 5.3, by passage through Sephadex G-25 (Pharmacia) at 5° C.

Longer and more rigid linkers, e.g. peptides with two attached maleimide groups, could be contemplated.

4. Upon emerging from the Sephadex column the Fc(mal)-containing solution is led onto the Phospho-Ultrogel 6B column, thereby eluting the bound antibody Fab (SH)$_5$ and yielding both proteins in a single concentrated solution (total protein about 10 mg/ml). The molar ratio Fc:Fab is three.

5. The reaction Fab(SH)$_5$+Fc(mal) is allowed to proceed at pH 5.3 and 20° C. for 16 hours. Residual SH groups are then removed by alkylation with N-ethyl-maleimide. Finally the products are separated, on the basis of size differences, by recycling chromatography through Sephacryl S-200HR (Pharmacia).

B. Using sacrificial FabFc from Subroutine (2)

The approach here is to prepare Fc(mal) and link it to antibody Fab(SH)$_5$ before removing the sheep Fab' gamma from the Fc. Steps 2 and 3 describe reduction and maleimidation at the Fc cysteine residue opposite that bonded to sheep Fab' gamma, keeping the pH low (4.0) so as to avoid reducing either the disulphide bond by which the sheep Fab' gamma is attached or the disulphide bond in the hinge.

1. As in A.

2. Sacrificial FabFc, in the form Fab-SS-Fc-SS-Py, is allowed to react with dithiothreitol (0.5 mM) at pH 4.0 and 5°, for one hour. It is thereby converted to Fab-SS-Fc-SH, which is separated on Sephadex G-25 equilibrated with pH 4.0 buffer.

3. The FabFc now reacts with 3 nm o-phenylenedimaleimide in 0.1M acetate, pH 4.0, 25% v/v dimethylformamide, at 5° C. for two hours. It is thereby converted to Fab-SS-Fc(mal) which is separated and concentrated by binding to a column of Phospho-Ultrogel 6B.

4. The two Phospho-Ultrogel columns (from stages 1 and 3) are eluted in series with 0.5M acetate, pH 5.3. The Fab-SS-Fc(mal) and Fab(SH)$_5$, at a molar ratio of 3:1, are allowed to react in concentrated solution (total protein about 12 mg/ml) for 16 hours at 25° C. The principal product is (Fab-SS-Fc)$_2$Fab.

5. The pH is raised to 6.0 and the proteins led through a column of Protein A-agarose, thereby binding all molecular species containing a human Fc component. Sheep Fab' gamma is now released from combination by passing 2 mM mercaptoethanol through the column at pH 6.0 for 30 minutes. Finally, to encourage re-formation of any hinge disulphide which may have been reduced, and to block the cysteine SH group left after release of the sheep Fab' gamma, 2 mM cystamine is passed through the column at pH 7.0 for 30 minutes.

6. Finally FabFc$_2$ and other products are separated, on the basis of size differences, by recycling chromatography through Sephacryl S-200HR (Pharmacia).

References

1. G. T. Stevenson, A. Pindar, C. J. Slade. A chimeric antibody with dual Fc regions (bisFabFc) prepared by manipulations at the IgG hinge. Anti-Cancer Drug Design 3:219–230, 1989.

2. K. Brocklehurst. Specific covalent modification of thiols: applications in the study of enzymes and other biomolecules. Internat. J. Biochem. 10:259–274, 1979.

FUNCTION

Figure 10:
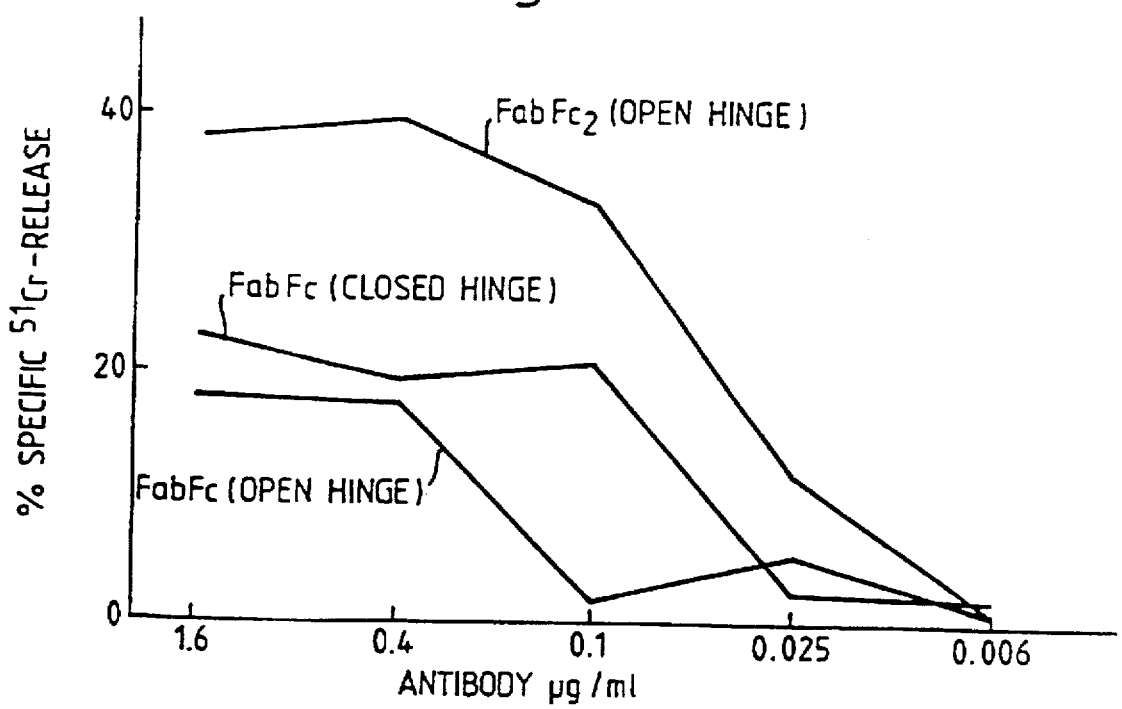
FIG. 10 is a graph of the killing of lymphoid cells by a derivative according to the invention compared with two other derivatives.

Preliminary assessments of function of FabFc$_2$ with parallel Fc moieties are illustrated with reference to FIG. 10 which is a graph plotting the killing of human lymphoid cells (Daudi-line, labelled with radioactive chromium) by three univalent chimeric antibody derivatives (specificity, anti-CD19) in the presence of human effectors (normal blood lymphocytes), effector: target=50). Cytotoxicity was measured after 3.5 hours at 37° C. A comparison is made of FabFc$_2$ (open hinge) with FabFc (open hinge) and FabFc (closed hinge), in this short-term test of antibody-dependent cellular cytotoxicity (ADCC), which is probably the best of those available in vitro for predicting the capacity of an antibody to kill target cells in vivo. The FabFc$_2$ is seen to be active in the test, and superior to its analogues containing only one Fc component.

Antibody derivatives have also been made in which the Fab region is derived from a monoclonal antibody having the following specifications.

Clone: WR17 (Obtainable from the Wessex Regional Immunology Service, Southampton, UK)

Isotype: Murine IgG2a

Fusion details: Conventional Kohler-Milstein type fusion using spleen cells from a Balb/c mouse immunised with cells from a patient with leukaemia and the mouse myeloma line NS—O.

Specificity: WR17 is an anti-CD37 reagent, reacting with a 40–52 kDa glycoprotein expressed strongly by B lymphocytes except in their early and late stages of development. This antigen is also weekly expressed by granulocytes and macrophages, and occasionally by T-cell lymphomas.

Applications: WR17 can be used as a primary antibody to detect CD37 +ve cells in suspensions and in frozen sections.

Preliminary indications of activity in an FabFc$_2$ derivative of this type were.

1. The FabFc$_2$ was seen by cytofluorimetry to bind to human B lymphocytes prepared from normal blood, and to the B-lymphocytic lines Namalwa and Daudi.

2. The FabFc$_2$ rendered Daudi cells susceptible to lysis by xenogeneic (guinea pig) complement, with 50% of plateau killing occurring at an antibody concentration of 1.6 micrograms/ml.

3. The FabFc$_2$ also rendered Daudi cells susceptible to ADCC by human blood lymphocytes, with 50% of plateau killing occurring at an antibody concentration of 50 nanograms/ml.

Further tests were also performed with an FabFc$_2$ derivative having its Fc components in serial configuration and comparing activity with an FabFc derivative. Mouse Fab' gammas and human Fc were used in each case. Experimental details were as follows:

The test concerned antibody therapy of a transplantable B-lymphocytic leukaemia (L$_2$C) of guinea pigs. $10^5$ cells were inoculated intraperitoneally into three groups of 8 animals on day 0. Treatment of two groups consisted of a single does of 0.2 mg antibody derivative, of anti-idiotype specificity, injected intraperitoneally at 24 hours. The control group of animals received phosphate-buffered saline (PBS). The doubling time of the tumour is approximately 19 hours, so on a simple kinetic basis each halving of tumour load prolongs life by a further 19 hours.

A graph of animals surviving plotted against days after inoculation showed the following:

1. PBS. A steep decline after 12 days to no survivors after 14 days.
2. FabFc. A slightly less steep decline after 15 days to no survivors after 20 days.
3. FabFc$_2$. A gradual decline after 15 days to 6 survivors after 20 days followed by a steep decline to one survivor after 21 days still surviving after 24 days.

I claim:

1. A chimeric antibody derivative of the formula:

where
Fc represents an Fc region;
R represents a synthetic chemical linkage group; and
Fab represents an Fab region.

2. The chimeric derivative of claim 1, wherein R is a divalent residue of dimaleimide of the formula:

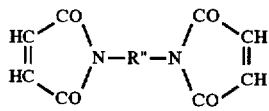

wherein:
R" is a divalent aryl or aliphatic group; and
Fab is an Fab region from a mouse monoclonal antibody specific for the CD37 differentiation antigen on human B-lymphocytes.

3. The chimeric antibody derivative of claim 1 in which one of said Fc regions has an open configuration.

4. The chimeric antibody derivative of claim 1 in which one of said Fc regions has a closed configuration.

5. The chimeric antibody derivative of claim 4 wherein the configuration is closed via bonding a synthetic chemical linking group.

6. The chimeric antibody derivative of claim 4 wherein the configuration is closed via a disulphide bond terminating at each end at a cysteine residue.

7. The chimeric antibody derivative of claim 3 wherein any free sulphydryl groups in the Fc regions have been rendered inert.

8. The chimeric antibody derivative of claim 1 wherein one of said Fc regions is derived from human immunoglobulin.

9. The chimeric antibody derivative of claim 1 wherein the Fab region is derived from monoclonal antibody.

10. The chimeric antibody derivative of claim 1 wherein the synthetic chemical linking group is a thioether linkage linked to a cysteine residue in the Fab region or an Fc region at one end, and to a cysteine residue in an Fc region at the other end of the linking group.

11. The chimeric antibody derivative of claim 1 wherein the synthetic chemical linking group comprises a residue of a divalent or trivalent linker molecule.

12. The chimeric antibody derivative of claim 11 wherein the residue is a divalent residue of a dimaleimide of the formula:

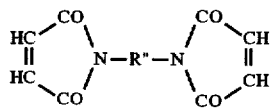

where R" is a divalent aryl or alkyl group.

13. The chimeric antibody derivative of claim 11, wherein the residue is a residue of a trivalent linker molecule linking the Fab region having two cysteine residues with an Fc region.

14. The chimeric antibody derivative of claim 13 wherein the residue is a residue of tris-2(2-chloroethyl)amine.

15. The chimeric antibody derivative of claim 1 wherein the synthetic chemical linking group contains a spacer molecule to increase the distance separating those parts of the antibody which are linked thereby.

16. The chimeric antibody derivative of claim 15 wherein the spacer molecule is derived from plasma albumin.

17. A diagnostic kit or test kit comprising the chimeric antibody derivative of claim 1.

18. A method of preparing the chimeric antibody derivative of claim 1 including the steps of:

(a) treating a first Fc region so as to provide as a reactive site thereon a residue of a synthetic chemical linking group; and (b) reacting the Fc region with a second Fc region via an intervening Fab region.

19. The method of claim 18 wherein the first Fc region is derived from an Fab Fc construct which has been produced by subjecting to thiol-disulphide interchange an intermediate product containing an open-hinge Fc region having a free sulphydryl group in the hinge region.

20. The method of claim 18, wherein an Fab region having more than one reactive site is reacted with a molar excess of Fc region to form an antibody derivative with two Fc regions linked via the Fab region.

21. A pharmaceutical composition comprising the chimeric antibody derivative of claim 1 with a pharmaceutically acceptable diluent or carrier.

22. A method of treating B-lymphocytic tumors comprising administering to a patient in need of same an effective amount of a chimeric antibody derivative of the formula:

Fc—R—Fab—R—Fc where
 Fc represent an Fc region,
 R represent a thioether linking group, and
 Fab represent an Fab region.

* * * * *